United States Patent [19]
Orejola

[11] Patent Number: 5,695,515
[45] Date of Patent: Dec. 9, 1997

[54] MITRAL VALVE DILATOR

[76] Inventor: Wilmo C. Orejola, 144 Mountain Ave., Pompton Plains, N.J. 07444-1020

[21] Appl. No.: 774,971

[22] Filed: Dec. 26, 1996

[51] Int. Cl.$^6$ .................................................. A61M 29/00
[52] U.S. Cl. ............................................ 606/191; 606/198
[58] Field of Search .................................. 606/191, 198, 606/194, 201; 623/1, 12

[56] References Cited

U.S. PATENT DOCUMENTS

| | | | |
|---|---|---|---|
| 5,320,634 | 6/1994 | Vigil et al. | 606/191 |
| 5,456,667 | 10/1995 | Ham et al. | 606/198 |

Primary Examiner—Michael Buiz
Assistant Examiner—Kevin Truong
Attorney, Agent, or Firm—Linval B. Castle

[57] ABSTRACT

A hydraulically operated surgical tool operated with video assistance through a small incision in a patient's chest for entering and expanding the mitral heart valve, The mitral valve dilator is a catheter-like element 4.5 cm, long and 8 mm, in diameter with a plurality of longitudinal arms that may be spread out to a 5 cm. diameter. The position of the arms is manually controlled by the application of pressure through a narrow flexible hydraulic control arm.

3 Claims, 5 Drawing Sheets

MITRAL VALVE DILATOR

This invention relates to surgical instruments and particularly to an instrument for opening a stenotic mitral heart valve through a small incision thoracoscope.

BACKGROUND OF THE INVENTION

For more than a hundred years modern medicine has known mitral stenosis as a clinicopathologic entity. The possibility of surgically relieving a blood flow obstruction through a narrowed mitral valve was suggested in 1902 but it wasn't until 1923 that such a procedure was attempted, and only one of seven patients survived the surgery. In 1948 the value of closed digital commissurotomy was shown to be effective and resulted in widespread adoption throughout the world. The technique was improved in 1959 with the use of the Tubbs mitral dilator. This gave more extensive commissurotomy than the digital technique until 1953 when it became possible to to open commissurotomy using a pump-oxygenator.

The classical procedure of closed mitral commissurotomy is approached through the left lateral thoracotomy. Through this incision the left atrial appendage is snared around the right index finger inserted into the mitral valve to examine and split apart the fused commissures. When unsuccessful, the transventricular Tubbs dilator is passed through an incision and at the apex of the left ventricle to more forcibly open the mitral valve. While this blind procedure had good results in highly selective patients, surgeons abandoned it for a safer open technique under cardiopulmonary bypass. Two frequently encountered hazards of using the Tubbs dilator were hemorrhage from laceration of the left atrium and cerebral embolism from thrombi in the atrium or calcific framents dislodged from the mitral valve. Another major downside of the procedure is the need for thoracotomy which has its own morbidity such as bleeding, post-operative pain, and infection. Nevertheless, for economic reasons this procedure is still prevalent in many developing countries.

Since 1960 various balloon techniques have been used in the treatment of cardiovascular deseases. And in 1984 a Japanese team of surgeons reported the use of a rubber balloon to open a stenotic mitral valve through the atrial septum. In comparison with the surgical mitral commissurotomy, this percutaneous balloon mitral valvuloplasty has the advantages of being done under local anesthesia, without cardiopulmonary bypass, and without thoracotomy. The procedure is being accomplished with success. In 1992 the National Heart Lung and Blood Institute Balloon Valvuloplasty Registry reported that a three-year study of the procedure showed a 1% mortality rate in the laboratory and a 5% 30-day mortality in 738 patients. Because of transseptal approach, iatrogenic ASD is an attending complication in more than 90% of successful percutaneous balloon mitral valvulvoplasty procedures. This spontaneously disappears but left-to-right shunting has been noted to persist in 10% of cases.

The percutaneous balloon undoubtedly is a better alternative to digital commissurotomy. However, because of iatrogenic ASD and its high incidence of persistent left-to-right shunting, this transseptal approach could be better served with left atrial appendage insertion of a flexible mitral valve dilator in conjunction with a video assisted thoracoscopy, An 8 mm. flexible dilator which can be hydraulically expanded to 50 mm. introduced into the heart through the appendage will not cause as much hemorrhage as the surgeon's finger in classical digital commissurotomy. And while thoracotomy is necessary to accommodate both hands of the surgeon inside the chest for the maneuvers, such major incisions would not be necessary using video guidance to insert the flexible mitral valve dilator into the heart. In addition, the video assisted thoracoscopic closed mitral commissurotomy (VATCMC) procedure being done in a hospital operating room should stand a better chance of survival than in the catheterization laboratory in the event of a cardiac emergency. Pregnant women may avoid fluoroscopy with transesophapeal echocardiography-guided VATCMC.

This VATCMC procedure addresses the concerns of hemorrhage, thoracotomy and post-operative morbidity. It may eventually reduce hospital stay to only a couple of days.

Briefly described, the mitral valve dilator of the invention is designed for video assisted thoracoscopic closed mitral commissurotomy. The dilator comprises a catheter-like element removeably coupled to the end of a long tubing. The dilator is 5 cm. in length and 8 mm. in diameter with three spring biased parallel blades which may be expanded outward from 8 mm. to about 5 cm. in diameter by hydraulic pressure applied through the tube. Using video assist the small dilator is maneuvered inside the chest and in to the stenotic mitral valve. The application of hydraulic pressure expands the blades of the dilator to force open the mitral valve.

DESCRIPTION OF THE DRAWINGS

In the drawings which illustrate the preferred embodiment of the invention.

DETAILED DESCRIPTION OF THE PREFERRED EMBODIMENT

The mitral valve dilator to be described is a hydraulically actuated unit on a flexible arm and is designed for video assisted thoracoscopic closed mitral commissurotomy. Its flexibility makes it easy to maneuver inside the chest and into the heart from outside of the body via small chest incisions or ports. It employs a mechanism that allows it to be inserted through the mitral orifice in a closed position and then opened to split apart fused commissures. It is introduced though the left atrial appendage through small incision thoracoscope and the opening and closing of the dilating mechanism is controlled by hydraulic pressure for a smooth, precise and long distance manipulation outside the chest.

Figure 1:
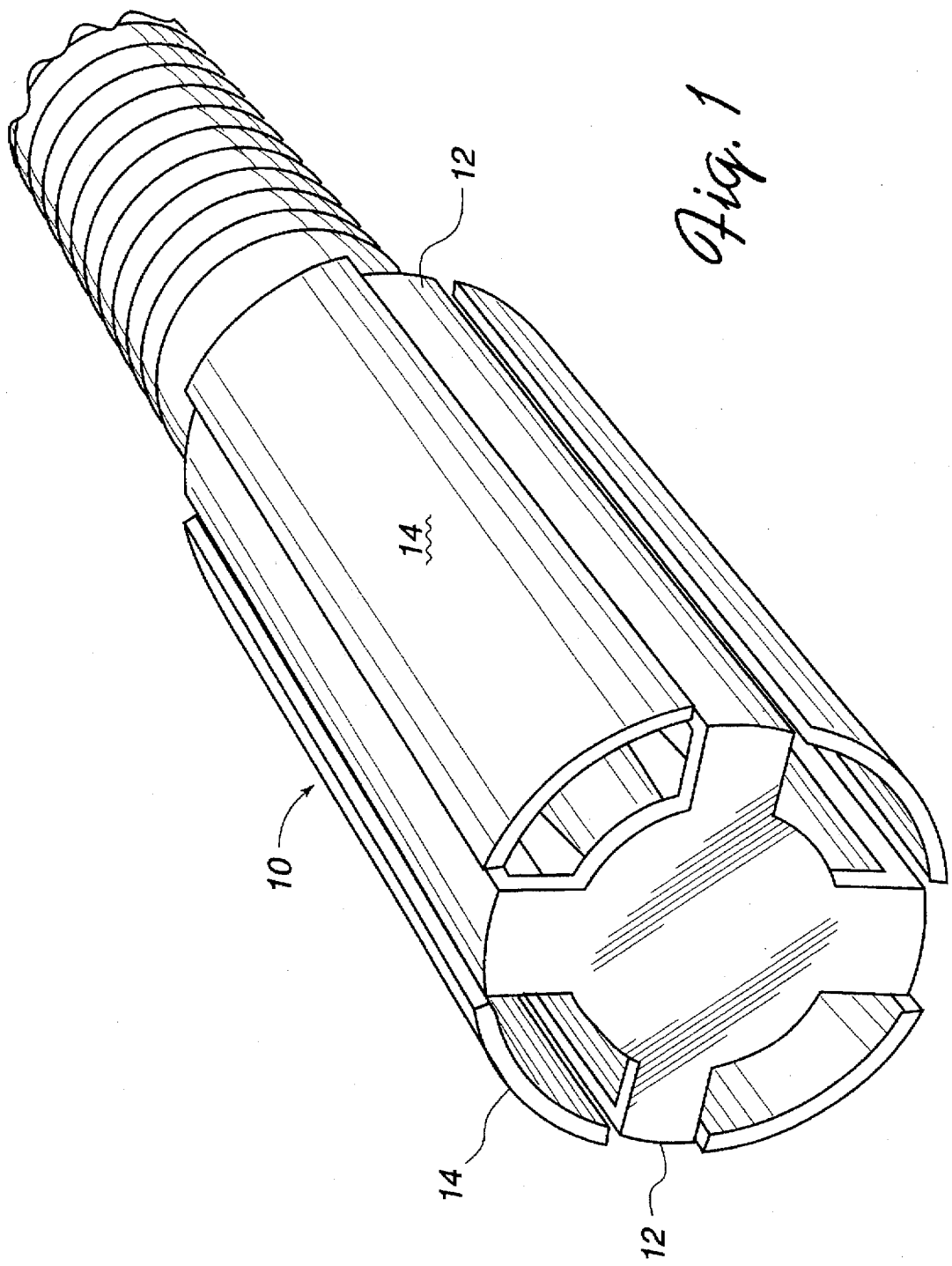
FIG. 1 is a perspective view of the closed mitral valve dilator.
Figure 2:
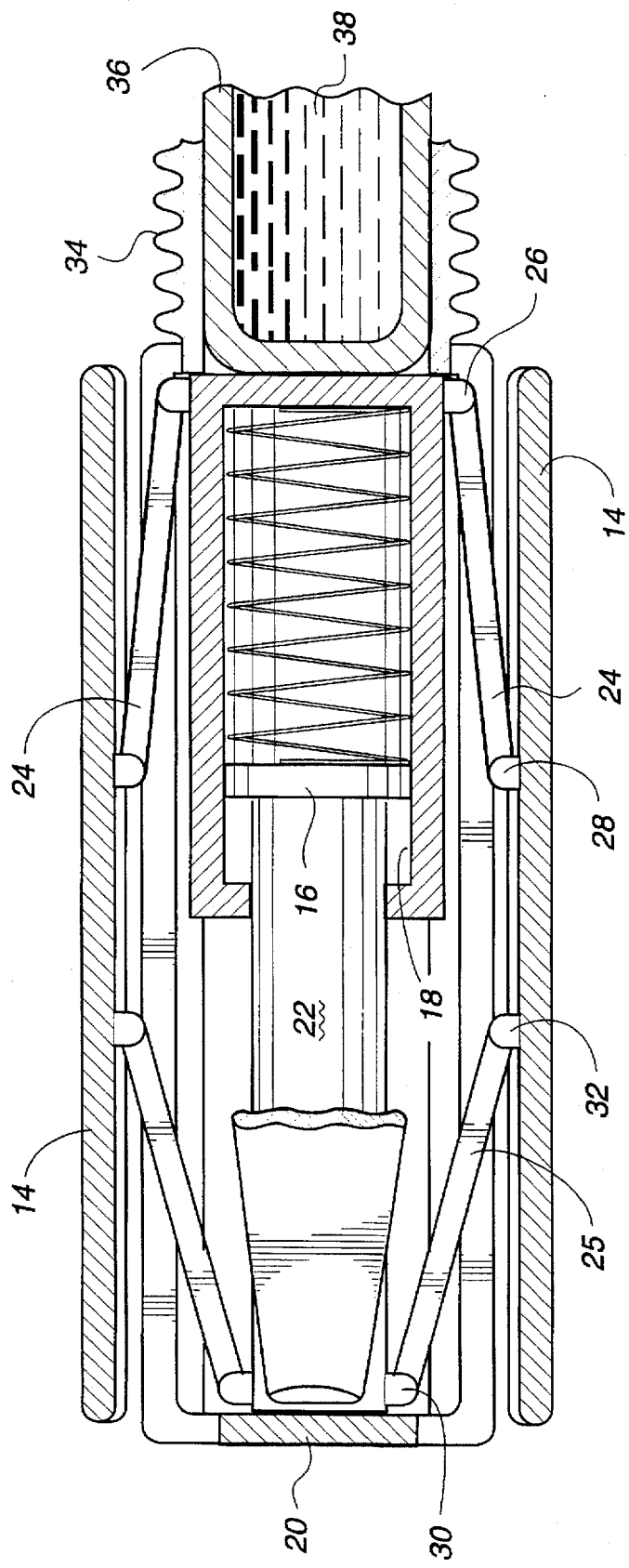
FIG. 2 is a sectional elevational view of the dilator showing an end portion of a flexible tubing.

FIG. 1 is a perspective drawing illustrating the dilator 10 starting to be opened. When completely closed, the catheter-like dilator has a smooth tubular exterior surface that is 8 mm. in diameter and 4.5 cm. in length. The tubular exterior surface is formed of four equally spaced longitudinal stationary segments 12 that form part of the body of the dilator 10 separated by four moveable longitudinal blades 14. The dilator 10 may be constructed of metal or plastic material.

The blades 14 of the dilator may be moved outward in unison into a diameter of approximately 5 cm. to expand a restricted mitral heart valve. At shown in the sectional elevational view of FIG. 3, this is accomplished with a piston 16 and cylinder 18 axially aligned within the dilator. The piston 16 is connected to interior end 20 of the dilator by a shaft 22, and the cylinder 18, the diameter of which occupies nearly the full open end of the dilator, is free to move axially upon the piston.

Pivotally attached to the exterior of the cylinder 18 are four equally spaced elevators 24 which are arms 2.0 cm. in length that extend from the pivot point 26 on the cylinder to a similar pivot point 28 on the moveable blades 14. Identical 2.2 cm. elevators 25 are connected from pivot points 30 on the interior end 20 of the dilator body to pivot points 32 on the moveable blades 14. Therefore, as the cylinder is pressed onto the piston, the elevators 24 will tend to force the blades 14 to move in the same direction as the cylinder, but the elevators 25 will hinder that movement with the result tht the blades move out and away from their original closed position.

A difference of 2 mm. between the length of the elevators 24 and 25 will correct for the difference in diameters of the pivots 26 and 30, respectively. This will result in the blades 14 being parallel when open.

For smoothest operation the dilator is operated by hydraulics. Its position is controlled by a flexible metal or plastic coil 34 which houses a sealed expandable plastic or rubber liner or sheath 36 that is filled with a non-expandable fluid 38. As pressure is applied to the sheath 36 from a remote position, the pressure is transmitted to the end of the cylinder 18 by the expandable sheath and the elevators 24, 25 react to force open the blades 14 of the dilator. As the pressure is released on the sheath 36, a spring 40 within the cylinder and acting against the piston 16 will return the cylinder to its original position and will withdraw the blades.

Figure 3:
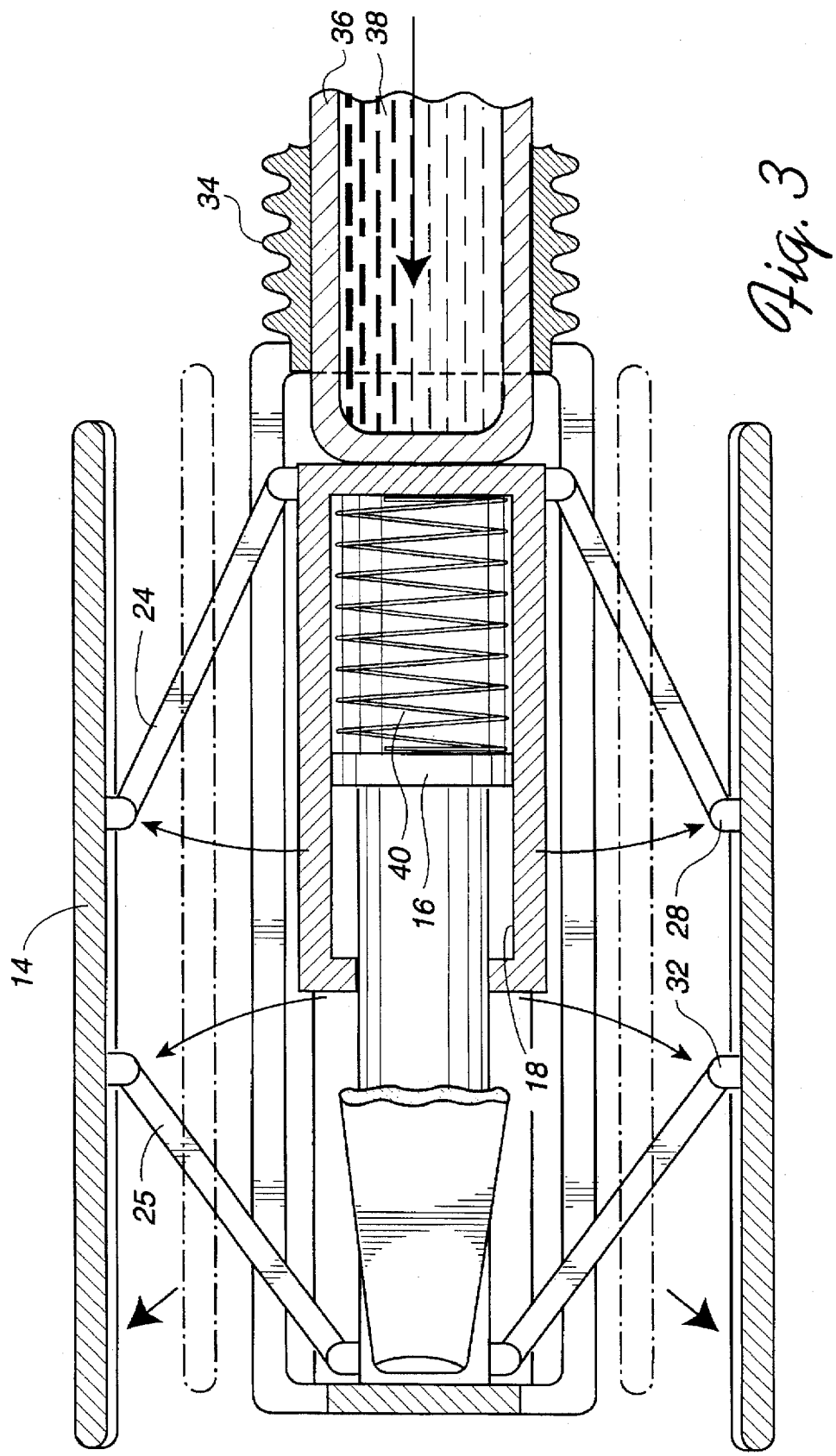
FIG. 3 is a sectional elevation view of the dilator partially expanded.

FIG. 3 is a sectional view illustrating the relative movement between the cylinder 18 and piston 16 and the resulting swinging out of the blades 24, 25 as the sealed sheath 36 pressure is increased.

Figure 4:
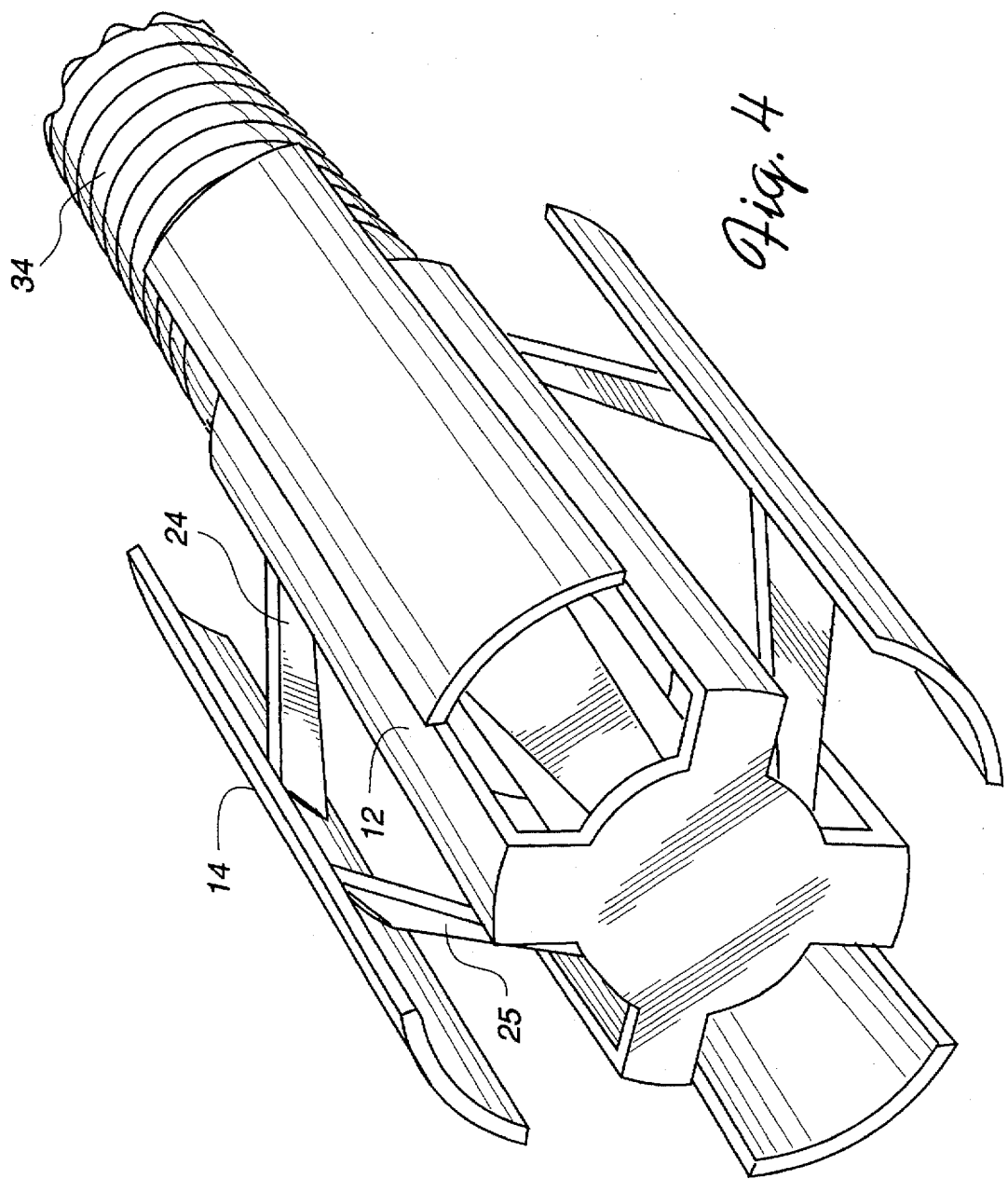
FIG. 4 is a perspective view of the partially expanded dilator.

FIG. 4 is a perspective view of the dilator 10 with the blades 14 partially extended and attached to a flexible arm 34.

Figure 5:
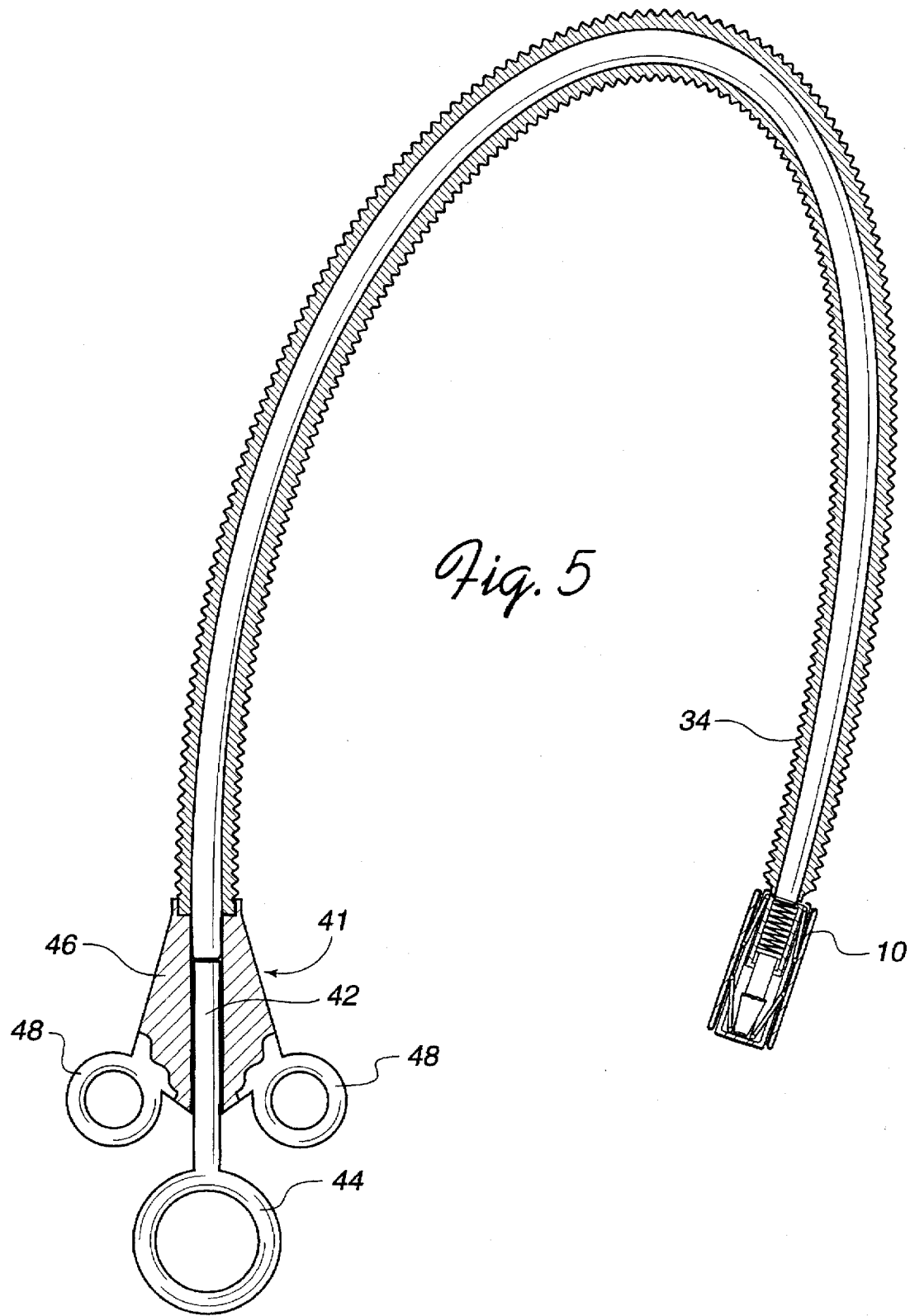
FIG. 5 illustrates the dilator coupled to a flexible arm with an operating handle, shown in section.

FIG. 5 illustrates the mitral valve dilator 10 and, in section, its flexible arm 34 and control handle 41. The flexible arm 34 is normally about 45 cm. in length. The control handle 41 is similar to a syringe in that it contains a piston 42 driven by a plunger with a finger ring 44 for the thumb, a body 46 and a pair of finger rings 48 on the body for the index and third finger. The index and third finger manipulate the dilator into position in the mitral valve and the thumb control the expansion of the blades.

I claim:

1. A surgical instrument manually operable from a remote distance, said instrument comprising:

a long tubular flexible arm having a first and a second end, said tubular arm containing a sealed expandable tubing, said expandable tubing being filled with a non-expandable fluid;

a manually operable means including a first piston coupled to the first end of said flexible arm, said first piston communicating with said sealed expandable tubing; and a cylindrical shaped assembly coupled to the second end of said flexile arm, said assembly having an interior containing an axial second piston and cylinder in communication with said sealed expandable tubing, an exterior surface of said assembly being smooth and partially formed by a plurality of blades pivotally coupled to said interior for concurrent movement from said exterior surface in response to relative movement between said axial second piston and cylinder.

2. The surgical instrument claimed in claim 1 wherein said manually operable means includes at least one finger ring coupled to said flexible arm and at least one moveable finger ring connected to said first piston for applying pressure and vacuum to said expandable tubing.

3. The surgical instrument claimed in claim 2 wherein said axial second piston and cylinder in said cylindrical shaped assembly reacts to the pressure applied by said first piston to extend and withdraw said blades to the surface of said cylindrical shaped assembly.

* * * * *